US007358076B2

(12) United States Patent
Hansen

(10) Patent No.: US 7,358,076 B2
(45) Date of Patent: *Apr. 15, 2008

(54) **SUBLANCIN LANTIBIOTIC PRODUCED BY *BACILLUS SUBTILIS* 168**

(75) Inventor: J. Norman Hansen, Silver Spring, MD (US)

(73) Assignee: The University of Maryland, College Park, MD (US)

( * ) Notice: Subject to any disclaimer, the term of this patent is extended or adjusted under 35 U.S.C. 154(b) by 405 days.

This patent is subject to a terminal disclaimer.

(21) Appl. No.: 10/372,098

(22) Filed: Feb. 25, 2003

(65) Prior Publication Data

US 2003/0166835 A1 Sep. 4, 2003

Related U.S. Application Data

(62) Division of application No. 09/462,478, filed as application No. PCT/US98/14547 on Jul. 17, 1998, now Pat. No. 6,541,607.

(60) Provisional application No. 60/053,035, filed on Jul. 18, 1997.

(51) Int. Cl.
*C12N 1/12* (2006.01)
(52) U.S. Cl. ............... 435/252.1; 435/7.1; 435/252; 435/7.32; 435/7.33; 435/7.34; 514/2; 514/12; 530/300; 530/350
(58) Field of Classification Search ............... 435/252, 435/252.1, 7.1, 7.32, 7.33, 7.34; 514/2, 12; 530/350, 300
See application file for complete search history.

(56) References Cited

U.S. PATENT DOCUMENTS 4,716,115 A    12/1987  Gonzalez et al. ........ 435/172.3

| | | | |
|---|---|---|---|
| 5,218,101 A | 6/1993 | Hansen | |
| 5,516,682 A | 5/1996 | Hansen | |
| 5,576,420 A | 11/1996 | Hansen | |
| 5,861,275 A | 1/1999 | Hansen | |
| 5,885,811 A | 3/1999 | Hansen | |
| 6,153,405 A * | 11/2000 | Hansen | ............... 435/69.1 |
| 6,541,607 B1 * | 4/2003 | Hansen | ............... 530/350 |

FOREIGN PATENT DOCUMENTS

WO    WO 00/39152    7/2000

OTHER PUBLICATIONS

Seffernick et al., J. Bacteriology, vol. 183, pp. 2405-2410, 2001.*
Wells, Biochemistry, vol. 29, pp. 8509-8517, 1990.*
Paik, S.H., et al., Isolation and Characterization of Chemical, Physical and Biological Properties of Sublactin 168, a novel Lantibiotic and the Cloning and Sequencing of the Structural Gene of Sublancin 168 and its Transporter Protein. Dissertation Abstracts Int'l (Jan. 1997), vol. 58, No. 11B, p. 5800.
Chakicerla, et al., "Role of the Leader and Structural Regions of Prelantibiotic Peptides as Assessed by Expressing Nisin-Subtilin Chimeras in *Bacillus subtilis* 168, and Characterization of Their Physical, Chemical, and Antimicrobial Properties", J. of Biol. Chem., Oct. 1995, vol. 270, No. 40, pp. 23533-23539.
Hansen, "Nisin and Related Antimicrobial Peptides", Biotechnology of Antibiotics, Second Edition, Revised and Expanded, pp. 437-467, 1997.
U.S. Appl. No. 60/215,449, filed Jun. 29, 2000, Hansen.

* cited by examiner

*Primary Examiner*—Hope Robinson
(74) *Attorney, Agent, or Firm*—Arent Fox LLP

(57) ABSTRACT

An antimicrobial peptide produced by *Bacillus subtilis* 168 was isolated and characterized and named sublancin 168. The invention includes DNA encoding for the sublancin 168 peptides and peptides which are at least 80% identical to the sublancin 168 peptide. The peptides may be administered as anti-bacterials, or may be used in food preservation. The peptides may also be co-administered with other lantibiotics (such as nisin and subtilin), or with known antibiotics.

7 Claims, 7 Drawing Sheets

Fig. 3

```
  1  attattaattcaaaataaatccataatagtcaatttattttagtgtattacaaccattctgtttattgatagtaataagttttttctatgattt 100  atgaacaagtttccttataatttcaaaaaaataaaaatatgttgaattagattatctttcttatattaaaaatgtaatccgattgcaaa
                                                              -35                       -10

199  caaatggggaggttttacaaatgaaaagctatttaagaagtaactagagaactcgaaaaccaaaaaggtagtggattaggaaaagctcagtgtg
                       r.b.s. SunA->M  E  K  L  F  K  E  V  K  L  E  E  L  E  N  Q  K  G  S  G  L  G  K  A  Q  C  A 298  ctgcgttgtgctacaatgtgctagtggcgtacaattggtgtgtggcgagctgttgctcaaactatcgtcaattctgcagataaacattt
      A  L  W  L  Q  C  A  S  G  G  T  I  G  C  G  G  G  A  V  A  C  Q  N  Y  R  Q  F  C  R  *

397  gtagagggaatatatttaaatattccctcatatttaaagcgggattgaaattgaataagaaaaagaaatatgttcatactaaacagtttaatagtcatg
                                                                     SunT--->  M  N  K  K  K  Y  V  H  T  K  Q  F  N  S  H  D 496  attgtggactagctgtatctcgtcaatttcataacctaagtttcataaccttaactatgaattgattcttactagacctaattgggataaggaaggctata
      I  V  D  *  L  Y  L  V  N  F  H  N  L  N  Y  G  I  D  F  L  L  D  L  I  G  D  K  E  G  Y  S 595  gtttaagagacttaattgttattttaagaagatgtgggataaaactaggccacttgattgcaagaaaataagacattcgaagcctaaacaaataa
      C  G  L  A  C  I  S  S  I  L  K  F  H  N  L  N  Y  G  I  D  F  L  L  D  L  I  G  D  K  E  G  Y  S
      L  R  D  L  I  V  I  F  K  K  M  G  I  K  T  R  P  L  E  L  Q  E  N  K  T  F  E  A  L  K  Q  I  K 694  agctcccttgtagctttgttagaagggggagaatatggacattacatacaataacgaattagaataactattacttgttagtgatcctgata ---->
      L  P  C  I  A  L  L  E  G  E  E  Y  G  H  Y  I  T  I  Y  E  I  R  N  N  Y  L  L  V  S  ---->
```

Fig. 4 prelantibiotic cleavage site ▷ leader peptide | prolantibiotic

Class AI

| nisin A | MSTKDFNLDLVS---VSKKDSG-ASPR | ITSISLCTPGCKTGALMGCNMKTATCHCSIHVSK |
| subtilin | MSKFDDFDLDVVK---VSKQDSK-ITPQ | WKSESLCTPGCVTGALQTCFLQTLTCNCKISK |
| epidermin | MEAVKEKNDLFNLDVKVNAKESN-DSG-AFPR | IASKFICTPGCAKTGSFNSYCC |
| pep 5 | MKNNKNLFDLEIKK-ETSQ-NTDELEPQ | TAGPAIRASVKQCQRTLKATRLFTVSCKGKNGCK | consensus leader
FNLDV  S  DS  PR
       D     T   Q

Class AII

| lacticin 481 | MKEQNSFNLLQEVTESELDLIIGA | KGGSGVIHTISHECNMNSWQFVFTCCS |
| streptococcin A-FF2 | MEKNNEVINSIQEVSLEELDQIIGA | GKNGVFKTISHECHLNTWAFLATCCS |
| salivaricin A | MNAMKNSKDILNNAIEEVSEKETMEVAGG | KRGSGWIATITDDCPNSVFVCC |
| cytolysin L1 | MENLSVVPSFEELSVEEMEAIQGS | GDVQAETTPVCAVATAAASSAACGWVGGGIFTGVTVVVSLKHC |
| sublancin 168 | MEKLFKEVKLEEIENQKGS | GLGKAQCAALWLQCASGGTIGCGGGAVACQNYRQFCR | consensus leader
EV  EL  GS
L   M   A

```
            0                                                              49
   SunT  MNKKKYVHTK QFNSHDCGLA CISSILKFHN LNYGIDFLL. .DLIGDKEGY
 LcnDR3       MKIVL QNNEQDCILA CYSMILGYFG RDVAIHELYS GEMI.PPDGL
consensus  MNKKK..... Q.N..DC.LA C.S.IL.... ....I..L.. ...I....G.
                       *

50                                                             99
   SunT  SLRDLIVIFK KMGIKTRPLE LQENKTFEAL KQIKLPCIAL LEGEEYGHYI
 LcnDR3  SVSYLKNINM KHQVSMHVYK TDKKNSPNKI FYPKMLPV.I IQWND.NHFV
consensus  S...L..I.. K......... .......... ...K...... .......H..
                                                                 *

100                                                           149
   SunT  TIYEI.RNNY LLVSDPDKDK ITKIKKEDFE SKFTNFILEI DKESIPEKEK
 LcnDR3  VVTKIYRKNV TLI.DPAIGK V.KYNYNDFM KKFSGYIITL SPNSSFTKKK
   PepT                                                      MK
consensus  ....I.R.N. .L..DP...K ..K....DF. .KF...I... ...S...K.K 150                                                           199
   SunT  DQKKHSYFFK DILFRNKLIV FVILLTSL.. ..FVVGLAVA GSFYIKFLVD
 LcnDR3  RISEIIFPLK KI.FKNR.NT FLYIF.SL.. ..FISQI.VA LWFSI.ILRD
   PepT  KENPLFFLFS KI.KWPK.SL FIIAI.IISS IGSITE.IIV PLLTG.NLID
consensus  ......f.fk kI.f.nk... F.i...sl.. ..fi....va ..f.i..L.D
```

Fig. 5

SUBLANCIN LANTIBIOTIC PRODUCED BY BACILLUS SUBTILIS 168

This is a division of U.S. patent application Ser. No. 09/462,478 filed Apr. 17, 2000, now U.S. Pat. No. 6,541,607, which in turn is a national stage entry of PCT Application No. PCT/US98/14547 filed Jul. 17, 1998, which claims the benefit of U.S. Provisional Patent Application No. 60/053,035 filed Jul. 18, 1997. The disclosures of the applications are hereby incorporated by reference herein in their entirety.

FIELD OF THE INVENTION

The invention relates to novel bacterially-produced antimicrobial peptides; more particularly the invention relates to a dehydroalanine-containing lantibiotic.

BACKGROUND OF THE INVENTION

Lantibiotics are bacterially-produced antimicrobial peptides that possess unique chemical and biological properties owing to their containing a variety of unusual amino acid residues. Lantibiotics are defined as such by the presence of lanthionine or β-methyllanthionine, which are introduced by a posttranslational process in which serine or threonine is dehydrated to the corresponding dehydro residue, which then reacts in a Michael-type addition of a cysteine sulfhydryl group to the double bond of the dehydro residue to form a thioether link [reviewed in (1-6)]. Mature lantibiotics typically contain one or more dehydro residues that do not participate in lanthionine bridges. The unique properties that are conferred by these unusual residues results in their being useful components in the design of novel biomolecules (1,2,7,8).

One of the attractive features of lantibiotics is that they are comprised of gene-encoded polypeptide sequences, so their structures can be manipulated by protein engineering. Whereas this is simple in concept, putting it into practice requires the utilization of many different genetic and recombinant DNA techniques, including the removal and replacement of chromosomal segments with their genetically-engineered counterparts. Ideally, these manipulations need to be done in such a way that the engineered lantibiotic analog be efficiently produced so that useful amounts of the analog are available for experimentation, which implies a need to engineer regulatory elements. Only a few bacterial strains have been sufficiently characterized to permit these manipulations to be performed in a convenient and facile manner. One such well-characterized bacterial strain is *Bacillus subtilis* 168, which is second only to *E. coli* in the extent to which tools of genetic and protein engineering have been developed, which has contributed to the extensive use of *B. subtilis* 168 for the industrial production of bio-engineered materials. The advantage of *B. subtilis* 168 over other bacterial strains has recently been increased even more by the availability of the complete sequence of the *B. subtilis* 168 genome (9).

SUMMARY OF THE INVENTION

The present inventor has discovered a new lantibiotic, named sublancin 168, that is a natural product produced by *B. subtilis* 168. Although approximately twenty lantibiotics are already known, the fact that this new lantibiotic is endogenous to *B. subtilis* 168, and thus can be studied and manipulated using the powerful methods that are available in this strain, suggests that progress in our understanding of lantibiotics will be accelerated by our ability to study and manipulate sublancin and the genes associated with its production in its natural *B. subtilis* 168 host. In addition to this practical aspect of the discovery, sublancin 168 has structural features and physical properties, such as the presence of disulfide bridges and extraordinary stability, that are unprecedented among the known lantibiotics.

Therefore, the present invention is directed to a peptide having an amino acid sequence which is at least 80% identical with SEQ ID NO: 7 prior to dehydration of serines and threonines and formation of thioether cross-linkages.

The invention also is directed to a peptide having an amino acid sequence which is at least 80% identical with SEQ ID NO: 5 prior to dehydration of serines and threonines and formation of thioether cross-linkages.

The invention is further directed to a peptide having an amino acid sequence which is at least 80% identical with SEQ ID NO: 18.

The peptides of the invention may be incorporated into a pharmaceutical preparation suitable for treating a bacterial infection. In addition, a bacterial-growth-inhibiting effective amount of one or more of the peptides of the invention may be added to a food for preservation against bacteria-mediated spoilage of the food.

The invention also includes a DNA which has a nucleic acid sequence which is at least 80% identical with SEQ ID NO: 4, preferably at least 80% identical with nucleotides 219-389 or nucleotides 447-782 of SEQ ID NO: 4, which includes the genetic sequence encoding the sublancin 168 peptide of the invention. More preferably, the DNA has a nucleic acid sequence which is at least 80% identical with nucleotides 219-389 of SEQ ID NO: 4.

The invention further includes a composition suitable for killing or inhibiting growth of bacteria, comprising the peptides of the invention and a carrier. Another composition encompassed by the invention comprises the peptides of the invention and a second active agent selected from the group consisting of a lantibiotic (such as nisin or subtilin) and an antibiotic.

BRIEF DESCRIPTION OF THE DRAWINGS

FIG. 3 shows the nucleotide sequence of the sublancin gene (SEQ ID NO: 4). The complete coding sequences of the sunA (SEQ ID NO: 5) and sunT (SEQ ID NO: 6) genes and their conceptual translations are available as Accession Number AF069294 in GenBank.

FIG. 4 shows the alignment of pre-sublancin with Type AI and Type AII prelantibiotics. Conserved leader segments of AI and AII as identified by Nes and Tagg (3). Sublancin shows homologies that are characteristic of Type AII lantibiotics, including the "diglycine motif" found in leaders that are normally cleaved by dual-function transporters that contain a leader peptidase function (20), as described in the (SEQ ID NOS: 8-15 and 5, respectively, in order of appearance).

FIG. 5 shows homologies of the N-terminal end of SunT (SEQ ID NO: 21) to PepT (SEQ ID NO: 17) and LcnDR3 (SEQ ID NO: 16), which are lantibiotic and dual-function transporters respectively.

DETAILED DESCRIPTION OF THE INVENTION

Figure 1:
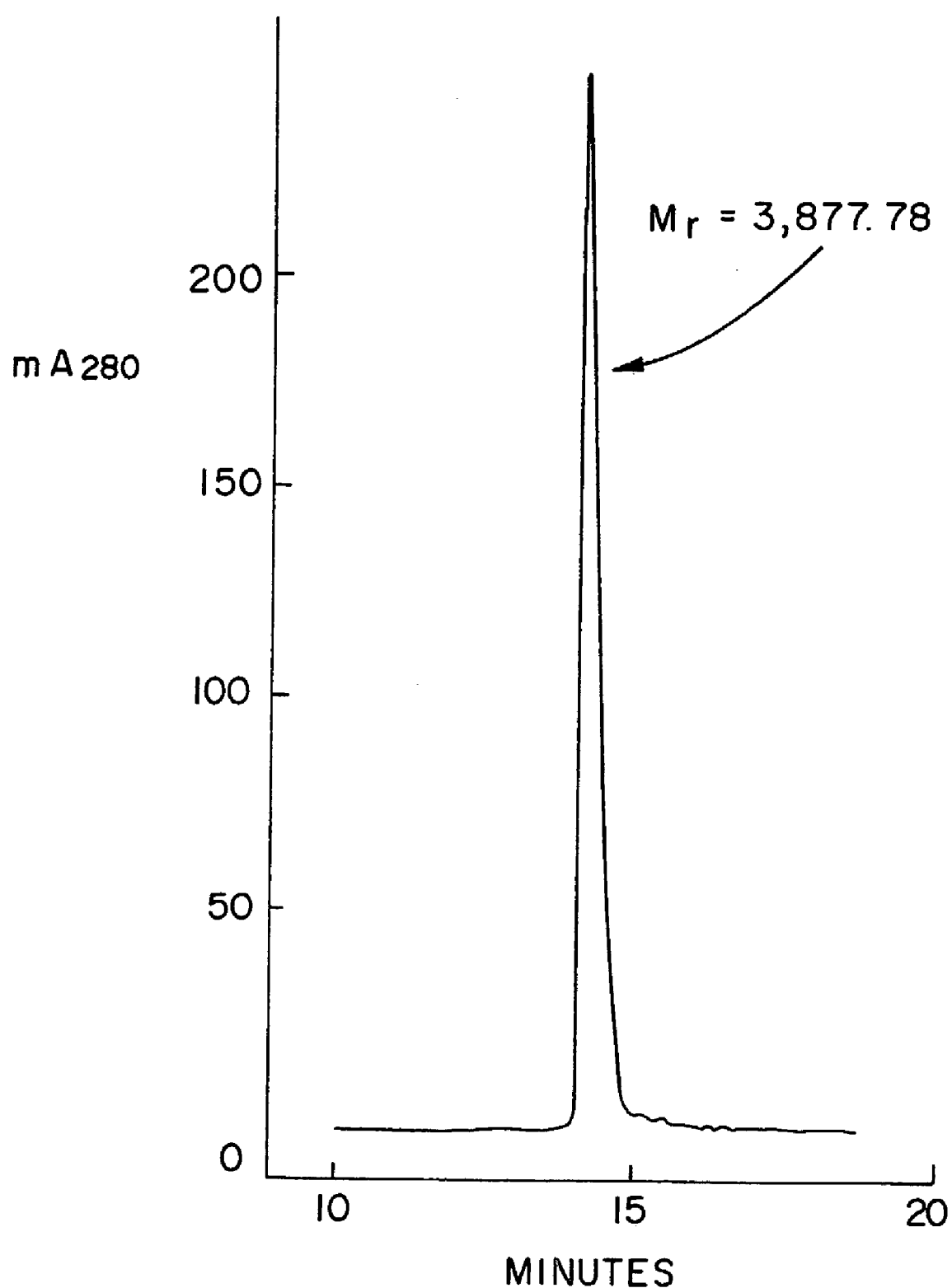
FIG. 1 shows the active peak of sublancin recovered from the supernatant using a hydrophobic interaction column and purified to near-homogeneity on a reversed-phase HPLC column. The active peak showed absorbances at 214, 254, and 280 nm.

The present invention is directed to a peptide having an amino acid sequence which is at least 80% identical with SEQ ID NO: 7 prior to dehydration of serines and threonines and formation of thioether cross-linkages. Preferably, the peptide contains the amino acids of positions 7, 14, 16, 19, 22, 29 and 36 of SEQ ID NO: 7. It is more preferred that a thioether cross-linkage is formed between the amino acids of positions 19 and 22 and disulfide cross-linkages are formed between the amino acids of positions 7 and 36 and positions 14 and 29. The peptide may preferably have an amino acid sequence which is at least 90% identical with SEQ ID NO: 7, most preferably, the amino acid sequence is 100% identical with SEQ ID NO: 7.

The invention is also directed to a peptide having an amino acid sequence which is at least 80% identical with SEQ ID NO: 5 prior to dehydration of serines and threonines and formation of thioether cross-linkages. Preferably, the amino acid sequence is at least 90% identical with SEQ ID NO: 5, most preferably, the amino acid sequence is 100% identical with SEQ ID NO: 5.

The invention is further directed to a peptide having an amino acid sequence which is at least 80% identical with SEQ ID NO: 18. Preferably, the peptide contains the amino acids of positions 7, 14, 16, 19, 22, 29 and 36 of SEQ ID NO: 18. It is further preferred that a thioether cross-linkage is formed between the amino acids of positions 19 and 22 and disulfide cross-linkages are formed between the amino acids of positions 7 and 36 and positions 14 and 29. The amino acid sequence is preferably at least 90% identical with SEQ ID NO: 18, most preferably 100% identical with SEQ ID NO: 18.

The invention also includes a DNA which has a nucleic acid sequence which is at least 80% identical with SEQ ID NO: 4, preferably at least 80% identical with nucleotides 219-389 or nucleotides 447-782 of SEQ ID NO: 4, which includes the genetic sequence encoding the sublancin 168 peptide of the invention. More preferably, the DNA has a nucleic acid sequence which is at least 80% identical with nucleotides 219-389 of SEQ ID NO: 4. The DNA sequence is preferably at least 90% identical with SEQ ID NO: 4 or the portions thereof disclosed above (i.e., nucleotides 219-389 and/or nucleotides 447-782), most preferably 100% identical.

All percentage identities for the amino acid and DNA sequences noted above can be determined using a variety of algorithms known in the art. An example of a useful algorithm in this regard is the algorithm of Needleman and Wunsch, which is used in the "Gap" program by the Genetics Computer Group. This program finds the alignment of two complete sequences that maximizes the number of matches and minimizes the number of gaps. Another useful algorithm is the algorithm of Smith and Waterman, which is used in the "BestFit" program by the Genetics Computer Group. This program creates an optimal alignment of the best segment of similarity between two sequences. Optimal alignments are found by inserting gaps to maximize the number of matches using the local homology algorithm of Smith and Waterman. It is preferred to use the algorithm of Needleman and Wunsch to compare amino acid and DNA percentage identity in the present case to another amino acid or DNA sequence.

FIG. 4 compares presublancin with the Type A lantibiotics, which are divided into two sub-types, AI and AII. The Type A lantibiotics include those that are the most thoroughly studied, such as nisin A, subtilin, epidermin, and Pep5. Type A lantibiotics are characterized by being elongated and cationic with molecular masses ranging from 2,151 to 4,635 Da (1). The mature region of the sublancin peptide is cationic, and its predicted molecular mass is approximately 3,900 Da (depending on what posttranslational modifications have occurred), and thus possesses characteristics of a Type A lantibiotic. Type AI and Type AII lantibiotics differ in their leader segments, with the AII leaders containing a GA/GS/GG ("double-glycine") sequence motif immediately preceding the cleavage site, and conserved EL/EV and EL/EM sequences upstream from the cleavage site. Double-glycine-type leader peptides are unrelated to the N-terminal sequences utilized by the sec pathway, and the corresponding ABC transporters typically possess a dual function that both removes the leader peptide and translocates it across the cytoplasmic membrane (20). These features are shared by several non-lantibiotic antimicrobial peptides, including pediocin and lactococcin A, which are produced by gram-positive bacteria; and by colicin V which is produced by gram-negative E. coli (20), suggesting that the double-glycine leader peptide may represent an evolutionary branch-point between the lantibiotic and non-lantibiotic peptides.

If the double-glycine leader peptide of sublancin is cleaved by a protease that is a component of a dual-function transporter, then the transporter should contain an identifiable protease domain. Examination of the ORF that is immediately downstream from the sunA gene shows that the putative SunT protein shows such a protease domain. FIG. 5 compares SunT with two other ABC-transporter proteins; PepT, which is the transporter for the Type AI lantibiotic Pep5 (which does not have a diglycine-type leader peptide), and with LcnDR3, which is the transporter for the non-lantibiotic lactococcin DR (which does have a diglycine-type leader peptide). The LcnDR3 protein contains an N-terminal protease domain that consistently appears in the dual-function transporters that cleave the leaders that-contain the diglycine motif (20), and this protease domain also appears in the SunT protein, and contains-the conserved cysteine and histidine residues that are part of the active site of the proteolytic domain.

The fact that the leader segment of sublancin contains that conserved features that are typical of Type AII lantibiotics constitutes evidence that sublancin is not only a lantibiotic, but is a Type AII lantibiotic. The SunT protein supports this conclusion by showing the presence of the protease domain that is expected for a transporter of a Type AII lantibiotic. Moreover, there is strong homology to PepT, which is a transporter of the lantibiotic Pep5, and lantibiotic transporters (LanT proteins) are generally conserved (2). All of these considerations are consistent with sublancin being a lantibiotic of the AII type.

The evidence that sublancin 168 is a lantibiotic is strong. The presublancin gene sequence encodes a serine residue at position 16 of the mature region, which can serve as the precursor to dehydroalanine. Sequential Edman degradation was blocked at position 16, which is characteristic of dehydro residues. As has been demonstrated for dehydro residues in other lantibiotics, the block was alleviated by derivatization with ethanethiol. Sequence analysis of the sublancin gene showed a leader segment with homologies to known Type II lantibiotics, including the "double-glycine" sequence motif immediately preceding the cleavage site, indicating that it is probably translocated by a dual-function ABC transporter that both translocates the peptide and proteolytically cleaves the leader segment. The gene immediately downstream from the sublancin gene confirms this, in that it encodes a protein that is homologous to known dual-function transporters, with an identifiable proteolytic domain in addition to a transporter domain. Although the presublancin gene encodes five cysteines, reaction of sublancin with an alkylating agent failed to demonstrate the presence of a free sulfhydryl group, which is consistent with at least one of the cysteines having reacted with a dehydrobutyrine residue to form a β-methyllanthionine bridge. The spectrum of activity of sublancin is similar to other lantibiotics in that it is active against a variety of gram-positive bacteria and inactive against gram negative bacteria. It also showed strong inhibition of bacterial spore outgrowth in addition to Inhibition of exponentially-growing cells, as is seen with both nisin and subtilin. However, unlike nisin and subtilin, washing sublancin-inhibited spores could cause a small percentage (about 1%) of them to proceed through outgrowth and then grow vegetatively, suggesting that the inhibitory effect of sublancin against spores is slightly reversible. For both nisin and subtilin, it has been demonstrated that the mechanism of inhibition of spore outgrowth is different from the inhibition of vegetative growth, in that an intact dehydroalanine is required for spore outgrowth inhibition, but not for vegetative growth inhibition. The fact that sublancin contains only one dehydro residue compared to the three dehydro residues in nisin and subtilin may account for sublancin showing reversibility of inhibition of spore outgrowth, whereas nisin and subtilin do not. It has been suggested that the dehydro residue can react with a nucleophilic target (2,27,29), in which case the larger number of possible attachment points of nisin and subtilin could reduce the likelihood of dissociation and reversal of inhibition, although this explanation is hypothetical.

With this report of the discovery and characterization of sublancin 168, the family of known lantibiotics increases in both size and scope, and there are now over 20 known lantibiotics (2). A striking feature of lantibiotics is their diversity in terms of structure, chemical properties, and biological properties (1,2). The defining characteristic of lantibiotics is that they contain the unusual amino acid lanthionine or β-methyllanthionine, which are formed by posttranslational dehydration of serine or threonine, respectively, followed by a Michael-type nucleophilic addition of a cysteine sulfhydryl across the double bond. Because of this mechanism, the presence of the lanthionine requires that the cell possess the machinery to dehydrate serines and/or threonines in addition to the ability to form the thioether linkage. Reflecting this, all the currently known lantibiotics possess at least one lanthionine and one dehydro residue in the mature peptide, although there is little reason to believe that exceptions to this are impossible. Especially notable is that, prior to my discovery of sublancin, all the cysteine residues in known lantibiotics had undergone posttranslational modifications, and never existed as disulfide bridges or free sulfhydryl groups. Sublancin breaks this trend in that only one of its five cysteines has been posttranscriptionally modified, and the other four cysteines instead participate in two disulfide bridges.

Lantibiotics can be considered as a subset of the prodigious number of ribosomally-synthesized antimicrobial peptides that have been discovered recently, many of which are produced by eukaryotic organisms, such as the defensins and cecropins (1,32). Mammalian and insect defensins, tachyplesins, and plant thionins all tend to be disulfide-rich, typically containing two or three disulfide bridges within a peptide consisting of 30-40 amino acid residues (33). The ubiquity and frequency of disulfide bridges argues an important role, perhaps by their ability to impose conformational constraints on the peptide and contribute to conformational and chemical stability. Because the thioether of the lanthionine bridge contains one sulfur atom instead of two, the lanthionine would be expected to be more conformationally-constrained than the disulfide. Moreover, the lanthionine is insensitive to redox conditions, while the disulfide is easily broken under mild reducing conditions. In view of the apparent superiority of the lanthionine bridge in terms of conformational and chemical stability, it is somewhat surprising that sublancin contains one lanthionine and two disulfides, instead of the three lanthionines and no disulfides that are found in other lantibiotics such as subtilin, which is produced by *Bacillus subtilis* ATCC 6633, and nisin. The fact that sublancin possesses both types of linkages suggests that having both types confers a selective advantage. It has been observed that antimicrobial peptides represent a remarkable example of convergent evolution, in which a wide variety of organism types have evolved antimicrobial peptides of common function from very different ancestral origins (33). Perhaps sublancin represents a converging evolutionary branch-point between prokaryotic lantibiotics and eukaryotic defensins, in which sublancin has taken advantage of both types of linkages.

The peptides of the invention may be incorporated into a composition suitable for killing or inhibiting growth of bacteria, preferably gram-positive bacteria. The peptides are provided in combination with a carrier. Suitable carriers are well known in the art. The processes of producing the compositions of the invention are well within the ordinary skill of a worker in the art, and will therefore not be described in detail.

Another useful composition of the invention comprises the peptides of the invention and another active agent, i.e., another lantibiotic or a known antibiotic. Nisin and subtilin are preferred lantibiotics. The combination of ingredients is quite effective when applied together to kill or inhibit the growth of bacteria, especially gram-positive bacteria.

The peptides of the invention may be incorporated into a pharmaceutical preparation suitable for treating a bacterial infection The peptides are provided in combination with a pharmaceutically acceptable carrier. Suitable pharmaceutically acceptable carriers are well known in the art. The processes of producing the pharmaceutical compositions of the invention are well within the ordinary skill of a worker in the art, and will therefore not be described in detail.

The invention includes a method of treating a bacterial infection in a patient in need thereof, comprising administering to the patient a bacterial-infection-treating effective amount of the peptides of the invention. The peptides may be administered by any acceptable route: oral, intravenous, intraperitoneal, topical, nasal, anal or vaginal. The dosage range contemplated is 0.01 to 1000 mg/kg body weight in 1-10 divided doses. Preferred dosages are 0.1 to 500 mg/kg body weight in 1-6 divided doses, more preferred 1.0 to 250 mg/kg body weight in 1-4 divided doses.

It is preferred that the bacteria to be treated is a gram-positive bacteria.

The invention also includes a method of inhibiting bacterial growth in a food, comprising adding to the food a bacterial-growth-inhibiting effective amount of the peptides of the invention. A preserved food, comprising a food and a bacterial-growth-inhibiting effective amount of the peptides, is also included in the invention. The amount of the peptides of the invention to be added are within the range of 0.001 to 1000 mg/kg of food, preferably 0.01 to 800 mg/kg of food, and more preferably 0.1 to 500 mg/kg of food.

It is preferred that the bacteria is a gram-positive bacteria.

The invention will now be described in reference to the following non-limiting examples.

EXAMPLE 1

Sublancin was isolated from *Bacillus subtilis* BR151, which is *B. subtilis* 168 (lys-3 metB10 trpC2), obtained from the Bacillus Genetics Stock Center, Ohio State University, Columbus Ohio. Stocks were maintained on agar with PAB (17.5 g BACTO® antibiotic medium 3 per liter). Sublancin was produced by inoculating 1 L of Medium A with 10 mL of BR151 cultured for 16 hr at 37° C. with vigorous aeration. Medium A is as previously described (10, 11), except it contained 2% sucrose instead of 10% sucrose. The culture was agitated vigorously by shaking 500 mL volumes at 200 rpm in 2 L baffled flasks at 37° C. for 28 hr, whereupon the culture usually acquired a pinkish-brown color, a fruity odor, and a pH that had dropped to about 6. Good sublancin production was consistently obtained when these events were observed. For reasons that are not understood, the color, odor, and pH changes did not always occur, whereupon sublancin production was usually poor. Similar variability has been reported for subtilin production in *B. subtilis* ATCC 6633 (10).

To isolate sublancin 168 the culture was acidified to pH 2.5 with concentrated phosphoric acid, and centrifuged to remove cells. The supernatant was made 1 M in NaCl and then applied, by a peristaltic pump, to a hydrophobic interaction column constructed with 25 ml of TOYOPEARL® Butyl-650 resin (TosoHaas, Montgomeryville, Pa.) that had been equilibrated with 1 M NaCl, 50 mM NaAc, pH 4. Unbound proteins were eluted with several volumes of the loading buffer, and the sublancin was eluted with 50 mM NaAc, pH 4.0; or alternatively, with 30% acetonitrile. After being lyophilized, the residue was dissolved in a minimum amount of water that contained 0.1% TFA, centrifuged to remove particulates, and applied to an analytical reverse-phase C-18 HPLC column (Rainin/Varian, Walnut Creek, Calif.) in a Hewlett-Packard 1050 HPLC machine with a diode-array detector. Sublancin was eluted using a 2-step gradient (solvent A was 0.1% TFA in water, solvent B was 0.1% TFA in acetonitrile), the first step going from 0 to 25% solvent B over 30 min, and the second step going from 25-35% solvent B over 30 min, using a 1.2 mL/min flow rate throughout.

Fractions in the second step were assayed for antimicrobial activity, active fractions were pooled, lyophilized, and then subjected to a second round of HPLC purification using the same conditions as the first round. The elution profile was monitored to detect the presence of peptide, dehydro residues, and aromatic residues, respectively. During the second round of HPLC purification, the activity was associated with a single absorbance peak; which was lyophilized and stored at −20° C. As shown in FIG. 1. the active peak showed absorbances at 214, 254, and 280 nm; and when the active peak was treated with ninhydrin, it gave the purple color that is characteristic of proteins and peptides. The antimicrobial substance was named sublancin 168, to connote its being an antimicrobial peptide that is produced by *B. subtilis* 168.

EXAMPLE 2

Two methods were employed to assay the activity of sublancin 168; a halo assay on plates, and a liquid assay in culture tubes. Both methods used *Bacillus cereus* T spores as the test organism. 250 mg of spores, prepared as previously described (12), were suspended in 30 mL of distilled water with a glass homogenizer, heat-shocked at 65° C. for 2 hr, centrifuged, and resuspended in 50% ethanol. This suspension was sprayed onto the surface of Medium A-containing agar plates using a Sigma spray unit (St. Louis Mo.). Prior to spraying, 10-20 μL volumes of serial dilutions of purified sublancin were spotted onto the plate. The plates were incubated at 37° C. for 5-12 hr to allow germination and growth of the spores, and the diameters of the halos caused by sublancin inhibition were measured, and the minimum amount of peptide that was required to give an observable halo was noted. For the liquid assay, heat-shocked spores were suspended in sterile water to a final concentration of 2 mg/mL, and then added to culture tubes containing 1% BACTO®-tryptone, 0.1 M TRIS®-Pi, pH 6.8. Prior to adding the spores, serial dilutions of sublancin were added to the tubes. The final concentration of spores was 0.1 mg/mL. The tubes were incubated at 37° C. for 3 hr, using sufficient shaking to keep the spores well suspended. The cultures were then examined using phase-contrast microscopy to observe the extent to which the spores had undergone germination, outgrowth, and vegetative growth. The amount of sublancin required to prevent the spores from proceeding through outgrowth was noted.

EXAMPLE 3

The lantibiotic family of antimicrobial peptides shows broad-spectrum activity against gram-positive bacteria, and very little activity against gram-negative bacteria (1,2). The ability of sublancin to inhibit growth of a variety of gram-positive and gram-negative bacterial strains was assessed using an agar-diffusion method, and for those strains that showed sensitivity to sublancin, a minimum inhibitory concentration (MIC) was determined. For the agar diffusion test, agar plates contained Difco brain heart infusion (*Listera monocytogenes, Lactococcus lactis, Enterococcus faecalis, Steprtococcus pyrogenes*) or Difco nutrient broth (*Bacillus cereus* T, *Bacillus megaterium, Bacillus subtilis, Staphylococcus aureus, Staphylococcus epidermidis, Bordetella bronchiseptica, Escherichia coli, Yersinia enterocolitica*). A 1,000-fold dilution of exponential cultures of the respective strains was made into molten top agar containing the appropriate medium, which was poured onto the agar plates. After solidification of the top agar, wells were made with an Ouchterlony punch and filled with a 20 μL (25 μg) of sublancin solution. The plates were incubated for 24 hr at 37° C., and the diameters of any halos of inhibition around the wells were measured. For those strains that showed a halo of inhibition, a MIC was determined by making a 100-fold dilution of an exponential culture of cells in tubes containing growth medium together with different concentrations (5, 10, 25, 50, or 100 μg/mL) of sublancin, which were incubated with shaking at 37° C. for 18-30 hr, until the respective control cultures without sublancin reached saturation. The MIC was that concentration of sublancin that completely suppressed growth of the cells.

Thus, the ability of sublancin to inhibit growth of the battery of gram-positive and gram-negative bacterial species was tested by the methods used by Cleeland and Squires (26) to evaluate the spectrum of activity of antimicrobial agents. As described Infra the strains were first assayed for susceptibility to sublancin in an agar-diffusion test. Next, the MIC for susceptible strains was determined in liquid culture. The results in Table I show that the antibiotic spectrum of sublancin is consistent with its being a lantibiotic, in that inhibition was observed only among gram-positive strains of bacteria. However, not all the tested strains of gram-positive bacteria were sensitive, and those that were sensitive varied considerably in their sensitivity to sublancin. Whereas *Bacillus megaterium* 14581 and *Bacillus subtilis* 6633 were inhibited by 5 µg/mL of sublancin, *Bacillus cereus* T and *Staphylococcus aureus* 12600 required more than 100 µg/mL for complete inhibition to occur.

TABLE 1

|  | sensitivity to sublancin | MIC (µg/mL) |
|---|---|---|
| gram positive strains | | |
| Bacillus cereus T | + | >100 |
| Bacillus megaterium (# 14581) | ++++ | 5 |
| Bacillus subtilis (# 6633) | ++++ | 5 |
| Enterococcus faecalis (# 19433) | – | |
| Lactococcus lactis (# 11454) | – | |
| Listeria monocytogenes (# 15313) | – | |
| Staphylococcus aureus (# 12600) | ++ | >100 |
| Staphylococcus epidermidis (# 12228) | – | |
| Streptococcus pyogenes (# 49399) | ++ | 100 |
| gram-negative strains | | |
| Bordetella bronchiseptica (# 10580) | – | |
| Escherichia coli JM101 | – | |
| Pseudomonas aeruginosa (# 10145) | – | |
| Yersinia enterocolitica (# 23715) | – | |

Strains were obtained from the American Type Culture Collection (ATCC) in Manassas, Va., and the ATCC strain numbers are indicated. Sensitivity to sublancin was determined by the agar diffusion test, and the degree of sensitivity was estimated from the diameter of the halo. (++++) indicates a halo diameter>200 mm, (+++) a diameter of 100-200 mm, (+) a diameter<60 mm, and (–) indicates no halo of inhibition. MIC values indicate the concentrations of sublancin that gave complete inhibition of cell growth in liquid culture.

EXAMPLE 4

The ability of sublancin to inhibit bacterial spore outgrowth was also determined. It had been earlier demonstrated that an intact $Dha_5$ residue in both subtilin (27) and nisin (28) is required in order for inhibition of bacterial spore outgrowth to occur. The fact that an intact $Dha_5$ residue its unnecessary to inhibit exponentially-growing cells established that the mechanism by which subtilin and nisin inhibit spores is different than the mechanism by which they inhibit growing cells (27). The ability of sublancin to inhibit bacterial spore outgrowth was tested using the same methods as for subtilin (27), which included a halo assay in which an agar plate was sprayed with a suspension of *B. cereus* T spores, and dilutions of sublancin were spotted onto the plate, which was incubated to permit the spores to germinate, outgrow, and grow exponentially to make a confluent lawn. Clear zones occur where the sublancin has been able to inhibit the development of spores into vegetative cells.

The other method was to incubate dilutions of sublancin with spores suspended in growth medium, and use phase-contrast microscopy to observe the stage of inhibition. The latter method established that sublancin permits the spores to germinate, to change from the phase-bright dormant state to the germinated phase-dark stage; whereupon further development (swelling, elongation, emergence, division) are inhibited (data not shown). In this liquid assay, the concentration of sublancin required to inhibit spore outgrowth was about 0.1 µg/mL, (27 nM) which is significantly less than the concentration of nisin (40 nM) or subtilin (80 nM) that is required to inhibit outgrowth of these same spores (27,29). It is notable that sublancin is about 1,000-fold more effective in inhibiting spore outgrowth than in inhibiting the same cells in exponential growth. The corresponding ratio for subtilin is 30-fold, which means that, although sublancin is slightly better at inhibiting spore outgrowth than is subtilin, subtilin is substantially better at killing the corresponding exponentially-growing cells than is sublancin. Using two or more lantibodies, optionally with one or more known antibiotics (e.g., sublancin and nisin; sublancin and subtilin; or sublancin, nisin and subtilin) in combination would thus be quite effective. The requirement for an intact $Dha_5$ residue in nisin and subtilin in order to exhibit sporostatic activity suggests that the $Dha_{16}$ residue of sublancin may also play an important role in the sporostatic processes.

While examining the halos caused by sublancin on the lawns of cells produced by spraying the plate with spores, we noted a discrepancy between the appearance of the halos produced by sublancin and the halos produced by either nisin or subtilin (data not shown). With nisin and subtilin, extended incubation of the plates for several days did not result in any change in the size or appearance of the halos, which remained completely clear. In contrast, incubation of the plates that contained sublancin halos resulted in occasional colonies growing up in within the halos, and a tendency for the surrounding cells to encroach across the perimeter of the clear zone, to cause the size of the halo to diminish slightly with time. The fact that the sublancin halos diminished in size whereas the nisin and subtilin halos did not, is explained by the relatively poor activity of sublancin against vegetative *B. cereus* T cells, so once the spores had developed into vegetative cells, they were able to encroach into the halo. However, the appearance of colonies within the clear zone suggested something else, which is that a small fraction of the spores that had been inhibited by sublancin at the post-germination stage were able to overcome this inhibition and proceed through outgrowth to the vegetative stage. If so, this is in contrast to nisin or subtilin, both of which have been shown to bind and inhibit spores irreversibly (30). To determine whether sublancin binding and inhibition to germinated spores is reversible, the *B. cereus* T spores were germinated for 3 hr in the presence of various concentrations of sublancin ranging from 0.1 to 100 µg/mL, centrifuging the inhibited spores out of the culture, and resuspending the spores in fresh medium without sublancin. The washed spores were then incubated for an additional 2-6 hr and examined by phase-contrast microscopy. Whereas most of the spores remained unchanged, a small percentage (about 1%) were clearly proceeding through outgrowth, and eventually reached the vegetative stage and proliferated. This result is consistent with the appearance of colonies within the halos on the plates, where the colonies represent those inhibited spores that recovered after the sublancin had diffused away. The concentration of sublancin used to treat the spores prior to washing had no effect on the outcome of the recovery experiment, with the 0.1 µg/mL treatment showing the same effect as the 100 µg/mL treatment. This shows that the spore sites to which the sublancin become associated are saturated at very low levels of sublancin.

EXAMPLE 5

Antimicrobial peptides that are chemically stable are better suited for practical applications than are unstable ones. The chemical stability of sublancin was therefore assessed when it was an unpurified component of the culture supernatant, and after it had been purified by HPLC chromatography. Activity was assessed using the agar-plate halo assay against bacterial spores. Culture supernatant stored at room temperature showed little change in halo size during the first four days, but showed significant loss after 1 week. Culture supernatants stored at either 4° C. or −20° C. showed no change in halo size after 6 months. HPLC-purified sublancin was remarkably stable, and one sample was stored as a 10 mg/mL solution of sublancin in sterile $D_2O$, pH 6.5, in an NMR tube for 2 years (protected from light); after which its activity remained undiminished and its NMR profile unchanged (data not shown). Sublancin was stable to a wide range of pH values when either phosphoric acid or ammonium acetate buffers were used to adjust the pH of culture supernatants over a range of 1.5 to 9.5. The samples were assayed after incubating them for 2 hr at 4° C. The pH 9.5 halo was diminished slightly, but the halos produced by the lower pH samples were unchanged. Finally, a sample of the culture supernatant that was autoclaved for 3 min at 121° C. showed undiminished activity. These stability characteristics resemble those of nisin, which is very stable at low pH and can survive autoclaving at pH 2.5 without damage, but is fairly unstable above pH 7 (31). However, the ability of sublancin to survive in aqueous solution, at a pH that is nearly neutral, for 2 years without any apparent chemical or biological degradation shows that it is a peptide whose intrinsic stability is extremely high. This extraordinary stability may prove to be a useful characteristic, perhaps enhancing the utility of sublancin in practical applications, or as a model compound whose study may inspire strategies for enhancing the stabilities of non-sublancin antimicrobial peptides.

EXAMPLE 6

Figure 6:
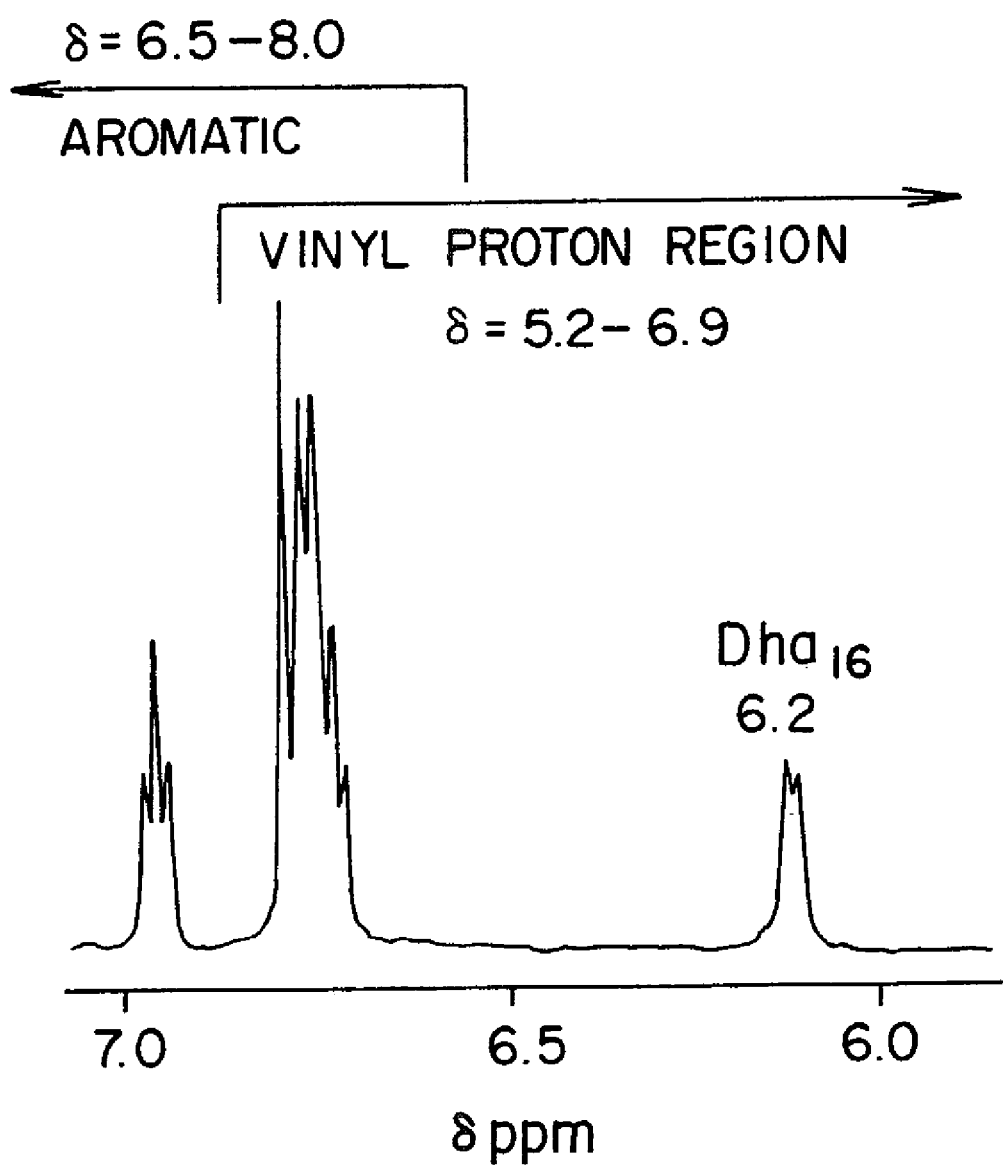
FIG. 6 shows the proton NMR spectrum of sublancin 168.

For sublancin to be a typical lantibiotic, it should contain at least one lanthionine residue, either Lan or MeLan; and at least one dehydro residue, either Dha formed from serine, or Dhb formed from threonine. The putative mature region of sublancin contains only one serine (residue 16), and one threonine (residue 19). For sublancin to contain at least one dehydro residue and one lanthionine residue would require that both the $Ser_{16}$ and $Thr_{19}$ be converted to $Dha_{16}$ and $Dhb_{19}$, respectively, and for one of them to form a cross-linkage with a cysteine, and for the other to remain as a dehydro residue. These possibilities can be distinguished by NMR spectroscopy. Both Dha and Dhb contain vinyl protons, which typically give resonance peaks in the δ=5.2-6.9 ppm region of the NMR spectrum, with Dha appearing as a doublet, and Dhb appearing as a quartet (7,21-23). The NMR spectrum of sublancin is shown in FIG. 6. A portion of the NMR spectrum shows a doublet appearing at δ6.2 ppm which is in the middle of the vinyl proton region, and therefore argues that a dehydro residue is present, and its being a doublet further argues that it is a Dha. The other peaks are in the aromatic proton region (δ=6.5 to 8.0), and can be attributed to the aromatic residues in sublancin. It is to be noted that the Edman degradation of native sublancin was blocked from residue 16 on, and this block was alleviated by reacting with ethanethiol, which is also consistent with residue 16 being a dehydro residue. Since the gene sequence shows a Ser at position 16, one can conclude that the Dha shown in the NMR spectrum is derived by post-translational dehydration of $Ser_{16}$ to $Dha_{16}$.

EXAMPLE 7

When sublancin was subjected to SDS-PAGE, it showed a single band that migrated at a position that corresponded to a molecular mass of approximately 4 kDa (data not shown). Ion-spray mass spectroscopy provided a more precise molecular mass of 3877.78 kDa as shown in FIG. 1. The sublancin molecular mass as predicted from the amino acid sequence encoded in the sublancin gene is 3713.3 Da, assuming one MeLan, one Dha, and four cysteines existing in two disulfide bridges. There is thus a discrepancy of 164.48 Da between this predicted molecular mass and the actual molecular mass, which may be due to one or more additional modifications of the amino acids.

Purified sublancin was sequenced from its N-terminal end using Edman degradation, using an Applied Biosystems (Foster City, Calif.) Model 477A peptide sequencer with an on-line HPLC analyzer in the Univesity of Maryland Core Facility (Baltimore, Md.). Amino acid composition analysis was performed on HCl hydrolysates by Commonwealth Biotechnologies, Inc. (Richmond Va.). Sublancin was treated with ethanethiol in order to sequence through any dehydro residues, which are otherwise blocked, using the method of Meyer, et al. (13). The modification mixture consisted of 280 µL ethanol, 200 µL sterile deionized water, 65 µL of 5 M NaOH, and 60 µL ethanethiol. 150 µL of this modification mixture was added to 50 µg of freeze-dried sublancin and incubated under nitrogen for 1 hr at 50° C. The pH was lowered by addition of 5 µL of glacial acetic acid, and the product purified by HPLC as described above for sublancin.

Sequence analysis using Edman degradation yielded a sequence of Gly-Leu-Gly-Lys-Ala-Gln-blank-Ala-Ala-Leu-Trp-Leu-Gln-blank-Ala-blank-blank-blank (SEQ ID NO: 19). The blank cycles were those that did not show an identifiable amino acid, some of which could be due to Cys residues, which were underivatized and therefore not detectable. Other potential sources of blank cycles are the unusual amino acid residues typically found in lantibiotics. For example, lanthionine residues do not produce peaks that are identifiable as normal amino acids, and the dehydro residues block the sequence analysis because they spontaneously lose their N-terminal amino group and are therefore unable to react with the Edman reagent (17), thus bringing the sequence analysis to a halt. This dehydro-residue block can be alleviated by reacting the peptide with ethanethiol, which adds across the double bond, thus preventing loss of the N-terminal amino group (13). Sublancin was accordingly derivatized with ethanethiol, whereupon it was possible to sequence past the apparent block at position 16, and to obtain Gly both at positions 17 and 18; but then a blank was encountered at position 19. The fact that ethanethiol derivatization alleviated the block at position 16 is strong evidence that residue 16 is a dehydro residue.

From DNA sequencing, it was determined that the sublancin prepeptide contains 5 cysteine residues, which is the same number of cysteines as are present in the prepeptides of nisin and subtilin. However, in nisin, subtilin, and all other known antibiotics, all of the cysteine residues are converted to unusual residues such as the 5 Lan and MeLan in nisin (24)and subtilin (11), or the aminovinylcysteine in epidermin (25). For a natural lantibiotic to contain unmodified cysteines or disulfide cross-linkages is unprecedented, so the cysteine residues in sublancin were examined to see if any possessed the characteristics of either free sulfhydryl groups or disulfide bridges. The amino acid analysis that was employed cannot detect free cysteine residues, but can detect them as carboxymethyl-cysteine if they are alkylated prior to acid hydrolysis. Alkylation of native sublancin followed by amino acid analysis gave no detectable carboxymethyl-cysteine, which rules out the presence of free sulfhydryl groups (data not shown). Reduction of sublancin with DTT followed by alkylation gave 3.3 (suggesting a real value of 4, since the 3.3 is likely a minimum value, and the nearest integer value larger than 3.3 is 4) carboxymethyl-cysteines per mole of sublancin. SDS-PAGE and ion-spray mass spectroscopy results described above established that sublancin exists exclusively as a monomer, so there cannot he any intermolecular disulfide bridges. These observations are all consistent with 4 of the cysteines of sublancin participating in two disulfide bridges, with the fifth cysteine having been converted to a MeLan residue by reacting with a Dhb residue (derived from post-translational dehydration of $Thr_{19}$), leaving the unreacted $Dha_{16}$ that is revealed in NMR spectrum.

One dimensional NMR spectroscopy was performed with a Bruker AMX-500 NMR spectrometer interfaced to an Aspect 3000 computer using UXNMR software. Lyophilized sublancin was dissolved in 99.96% atom % $D_2O$ to exchange protons and lyophilized (done twice) and dissolved in $D_2O$ to a final concentration of 10 mg/mL. The proton spectra were recorded at constant 295° K. in $D_2O$ with and without the suppression of the water solvent resonance. Mass spectral analysis was performed by PeptidoGenic Research & Co (Livermore, Calif.) on a Sciex API I Electrospray mass spectrometer. The reported masses are those calculated as the most probable values based on the different m/z forms.

The NMR spectrum of sublancin showed a doublet in the vinyl proton region of the spectrum, which is consistent with the presence of a dehydroalanine.

EXAMPLE 8

Figure 7:
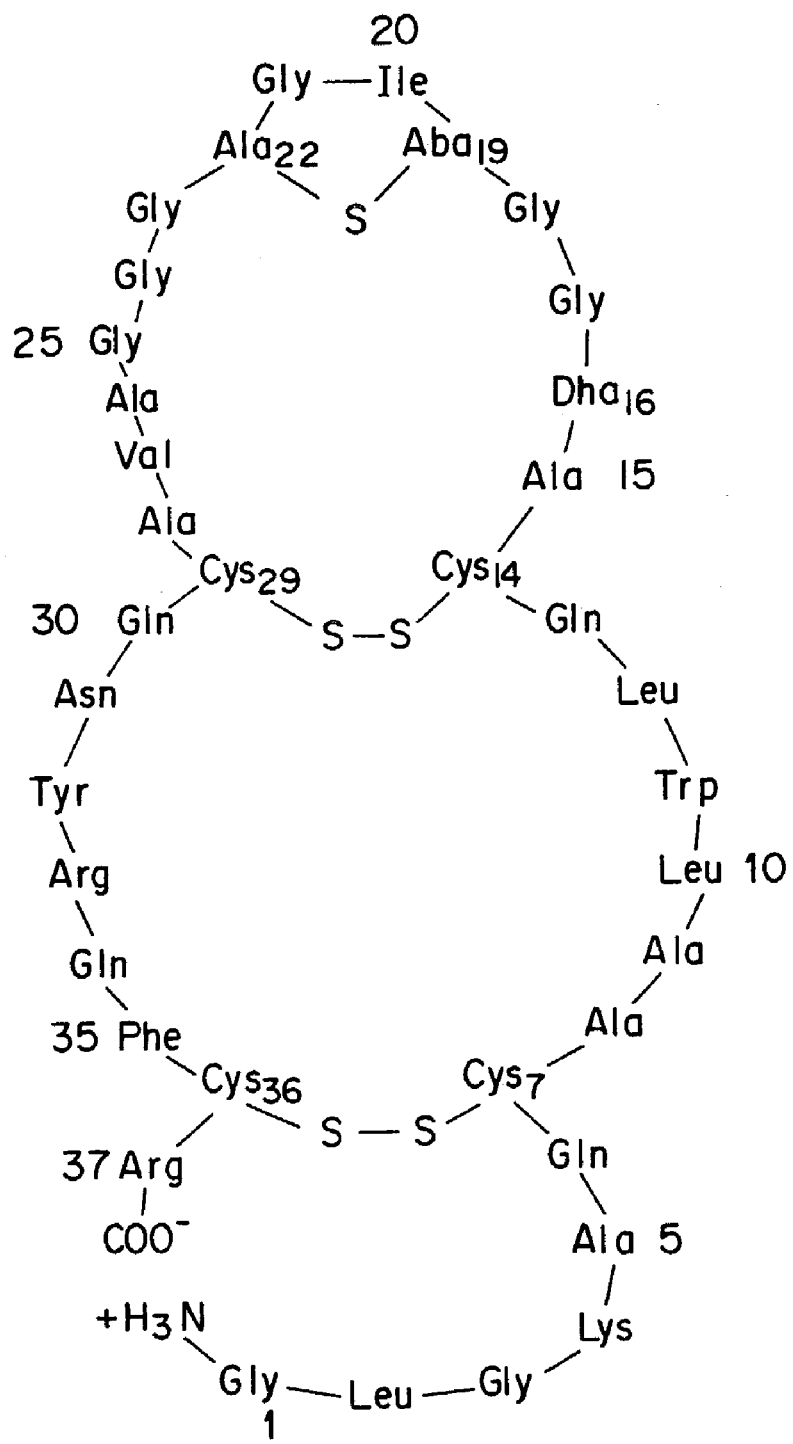
FIG. 7 shows the locations of thioether and disulfide bridges in sublancin 168 (SEQ ID NO: 18).

The number and location of disulfide bridges was further explored by analysis with. proteolytic enzymes. The native form of sublancin, and the denatured form, and the denatured-reduced form of sublancin were all resistant to trypsin, despite the presence of a Lys at position 4 and an Arg at position 33. When the denatured and reduced sublancin was alkylated, trypsin cleavage gave detectable amounts of fragments of 3,200 and 1,581 Da, neither of which is an expected product. Sublancin was more sensitive to chymotrypsin, with even the native molecule being substantially degraded, to give products of 1,392 and 1,823 Da. The first is consistent with a polypeptide consisting of residues 1-11 being cross linked by a disulfide bridge to a peptide consisting of residues 36-37 ($G_1$-$W_{11}$-S-S-$C_{36}$-$R_{37}$, with an expected value of 1,392 Da) and the second is consistent with a polypeptide consisting of residues 1-11 cross linked by a disulfide bridge to a peptide consisting of residues 33-37 ($G_1$-$W_{11}$-S-S-$R_{33}$-$R_{37}$, with an expected value of 1,823 Da); with chymotrypsin having cleaved at typical major cleavage sites ($W_{11}$, $Y_{32}$, $F_{35}$,). From this, we can conclude that native sublancin has a disulfide bridge between $Cys_7$ and $Cys_{36}$. To decide upon the location of the second disulfide bridge, we compare sublancin to other Type A lantibiotics, and note that formation of a thioether link between $Cys_{22}$ and $Dhb_{19}$, to give a $Aba_{19}$-$Ala_{22}$ MeLan-type cross-linkage would put a 2-residue $Gly_{20}$-$Gly_{21}$ sequence in the ring enclosed by the MeLan cross-link, which is similar to the 2-residue Prog-$Gly_{10}$ sequence enclosed by the $Aba_8$-$Ala_{11}$ MeLan cross-link in both nisin and subtilin. Moreover, formation of this particular MeLan bond is consistent with the observation that the Cys-Dha partner selection in lantibiotics consistently involves a dehydro residue that is on the N-terminal side of the Cys residue. Assuming that the MeLan that actually forms conforms to these standard patterns, then $Cys_{22}$ will react with $Dhb_{19}$, which would require the second disulfide bridge to form between $Cys_{14}$ and $Cys_{29}$, as shown in FIG. 7.

EXAMPLE 9

Figure 2:
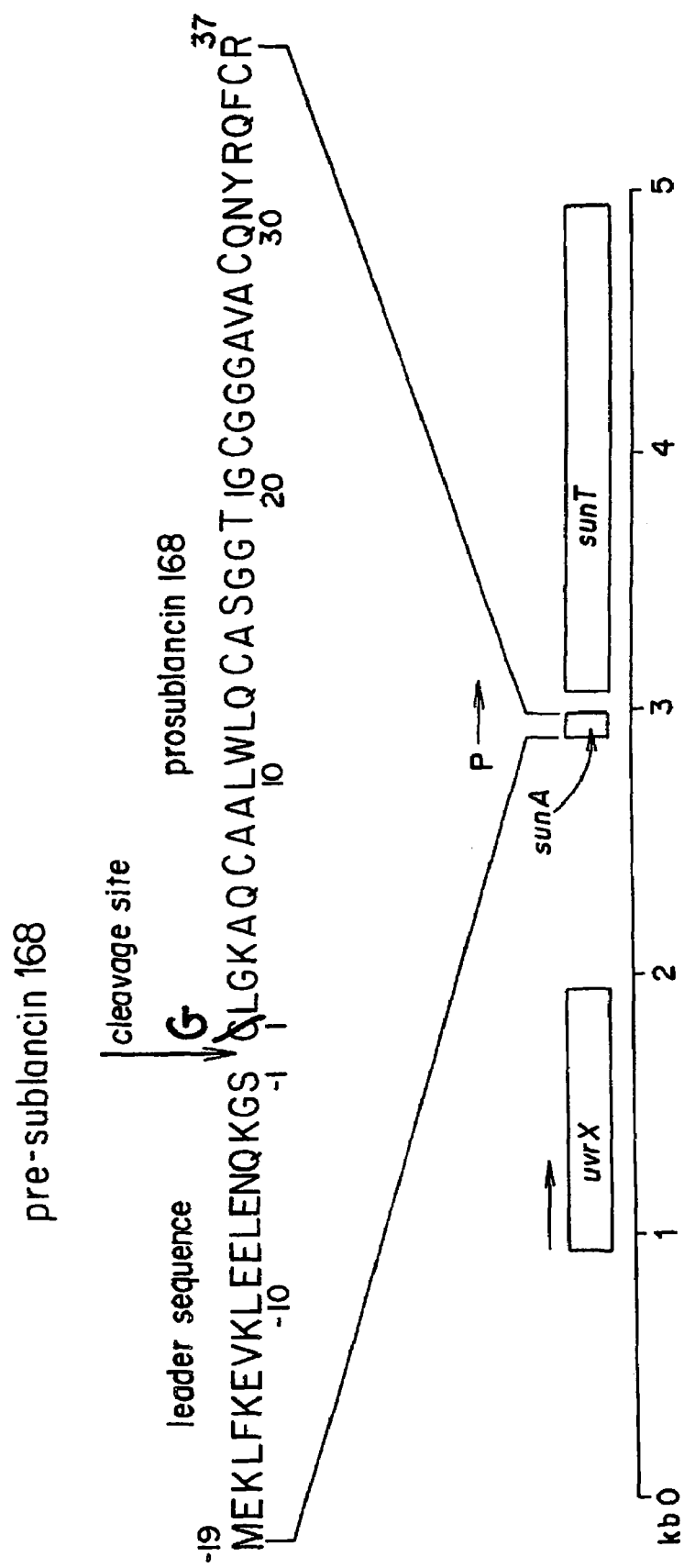
FIG. 2 shows the sequence of presublancin 168 (SEQ ID NO: 20). The P indicates the location of a consensus prokaryotic promoter site as described in the legend of FIG. 3. (Prosublancin sequence disclosed as SEQ ID NO: 7)

Since lantibiotics are biosynthesized from gene-encoded precursors, one approach to determine if sublancin is a lantibiotic is to see if it is gene-encoded, and if it is, to examine the gene and the operon in which it is found to see if they possess features that are characteristic of lantibiotics. To determine whether sublancin is a gene-encoded peptide, the N-terminal sequence was used to design a hybridization probe, which was then used to screen a *B. subtilis* 168 genomic library that had been constructed in bacteriophage λ. Clones containing positive signals were subjected to DNA sequence analysis. Nearly 5 kb of sequence was obtained, which we published in a public database as soon as it was complete (18). This sequence was searched for open reading frames (ORFs), which were in turn searched for the N-terminal amino acid sequence of sublancin 168. A 56-residue ORF, shown in FIG. 2, that contained a perfect match to the N-terminal sequence of the sublancin peptide was found near the center of the 5 kb sequence. In addition, a 332-residue ORF was found upstream from the sublancin gene, and about 560 residues of a partially-complete ORF was found downstream from the sublancin gene. The locations of these three ORFs within the 5 kb sequence are shown in FIG. 2. Several months after our sequence was published in GenBank, the Bacillus Genome Project published the complete *B. subtilis* 168 genome (9), which mapped these genes at a position of 193.80° on the *B. subtilis* 168 chromosome.

The putative functions of the upstream and downstream ORFs were explored by searching the GenBank/EMBL nucleotide databases for homologies to proteins with known functions. The 332-residue upstream ORF (denoted uvrX) showed extensive homologies to proteins involved in repair of u.v. damage to DNA, so a role in the biosynthetic pathway of sublancin seems unlikely. The 560-residue segment of the downstream ORF showed homologies to known ABC transporter proteins including PepT, which is the transporter that is responsible for secretion of Pep5 during its biosynthesis (19). The gene for this downstream ORF (denoted sunT) is therefore a strong candidate as the corresponding transporter that participates in the secretion of sublancin. FIG. 3 shows the segment of the DNA sequence that contains the sublancin gene (sunA), and the 5-prime end of sunT, together with their conceptual translations (sunA and the N-terminal portion of sunT), the putative promoter region of the sun operon, and the ribosome binding site of the sunA mRNA. The complete sequences and their conceptual translations are available as Accession Number AF069294 in GenBank.

EXAMPLE 10

A *B. subtilis* 168 genomic library was constructed in bacteriophage lambda using total chromosomal DNA from strain BR151 grown in 50 mL of PAB. Cells were lysed with a mixture of lysozyme, sodium dodecyl sulfate, and proteinase K; and the DNA was recovered and deproteinized with phenol-chloroform as previously described (11). The genomic DNA was partially-digested with Sau 3Al to give random fragments in a 12-23 kb size range, which were cloned into LambdaGEM-12 partially filled-in Xho I half-site arms obtained from Promega (Madison, Wis.), which were then packaged into *E. coli* cells using the protocol provided by the manufacturer. The library was screened for the sublancin gene using synthetic DNA oligomers whose sequences were chosen using the strategy of Lathe (14), based on the 16-residue N-terminal sequence of sublancin. Three single-sequence 48-mer probes were designed, each one with randomly-chosen degenerate bases, and the synthesis was performed by Ransom Hill Bioscience (Ramona Calif.). For those amino acid residues that appeared as unidentifiable blanks in the sequence, inosines were placed in the corresponding codons in the probes. The three probes were:

Probe 1 (SEQ ID NO:1):
GGGTTGGGTAAAGCCCAAIIIGCGGCCTTGTGGTTACAGIIIGCTTCC

Probe 2 (SEQ ID NO:2):
GGGTTGGGCAAAGCACAGIIIGC- GGCTTTTTGGTTACAGIIIGCGTGC

Probe 3 (SEQ ID NO:3):
GGACTTGGTAAAGCGCAAIIIGCAGCTCTGTGGCTTCAAIIIGCATG- C.

The probes were radio-labeled with $^{32}$P at their 5-prime ends using T4 polynucleotide kinase and hybridized to Southern blots of restriction digests of BR151 genomic DNA under a variety of temperature and ionic strength conditions in order to optimize the signal strength and specificity. Probe 1 gave a good signal when hybridized at 45° C. in 6×SSC and washed at 37° C. in 2×SSC; whereas probe 3 gave a good signal when hybridized at 45° C. in 6×SSC and washed at 45° C. in 2×SSC. A good signal for probe 2 could not be obtained, so its use was abandoned. The bacteriophage λ library was plated and transferred to duplicate nitrocellulose filters using standard procedures (15). One of the duplicate filters was hybridized to probe 1, and the other to probe 3. The only plaques selected for further study were those that hybridized to both probes. Several such dual-hybridizing plaques were picked, their inserts were subcloned into pTZ plasmids and screened again with probes 1 and 3. Positive inserts were cloned into M13 and subjected to dideoxy sequence analysis. The DNA sequences were conceptually translated into six reading frames, which were searched for the N-terminal amino acid sequence of sublancin. When the sublancin sequence was found, the actual DNA sequence that encoded the sublancin gene could be identified, which provided the sequence information needed to synthesize probes that were exactly homologous to the sublancin gene. These were used to identify library clones that contained sequences that surrounded the subtilin gene, which were then also subcloned and sequenced.

REFERENCES

1. Hansen, J. N. *Ann. Rev. Microbio.* (1993) 47, 535-564.
2. Hansen, J. N. (1997) in *Biotechnology of Antibiotics*, Second ed. (Strohl, W. R., ed) pp 437-470, Marcell Dekker, Inc.: New York,
3. Nes, I. F., Tagg, J. R. *Antonie Van Leeuwenhoek* (1996) 69, 89-97.
4. Sahl, H.-G. (1994) in *Antimicrobial Peptides. Ciba Foundation Symposiu6* (Marsh, J., Goode, J. A., eds), pp 27-53, John Wiley & sons Ltd: Chichester, England,
5. Sahl, H. G., Jack, R. W., Bierbaum, G. *Eur. J. Biochem.* (1995) 230, 827-853.
6. de Vos, W. M., Kuipers, O. P., Vandermeer, J. R., Siezen, R. J. *Mol. Microbiol.* (1995) 17, 427-437.
7. Liu, W., Hansen, J. N. *J. Biol. Chem.* (1992) 267, 25078-25085.
8. Chakicherla, A., Hansen, J. N. *J. Biol. Chem.* (1995) 270, 23533-23539.
9. Kunst, F., Ogasawara, N., Moszer, I., Albertini, A. M., Alloni, G., Azevedo, V., Bertero, M. G., Bessieres, P., Bolotin, A., Borchert, S., Borriss, R., Boursier, L., Brans, A., Braun, M., Brignell, S. C., Bron, S., Brouillet, S., Bruschi, C. V., Caldwell, B., Capuano, V., Carter, N. M., Choi, S. K., Codani, J. J., Connerton, I. F., Danchin, A., et al. *Nature* (1997) 390, 249-256.
10. Feeney, R. E., Garibaldi, J. A., Humphreys, E. M. *Arch. Biochem. Biophys.* (1948) 17, 435-445.
11. Banerjee, S., Hansen, J. N. *J. Biol. Chem.* (1988) 263, 9508-9514.
12. Vary, J. C., Halvorson, H. O. *J. Bacteriol.* (1965) 89, 1340-1347.
13. Meyer, H. E., Heber, M., Eisermann, B., Korte, H., Metzger, J. W., Jung, G. *Anal. Biochem.* (1994) 223, 185-190.
14. Lathe, R. *J. Mol. Biol.* (1985) 183, 1-12.
15. Maniatis, T., Fritsch, E. F., Sambrook, J. (1982) *Molecular Cloning. A Laboratory Manual*; Cold Spring Harbor Laboratory, Cold Spring Harbor, N.Y.
16. Liu, W., Hansen, J. N. *J. Bacteriol.* (1991) 173, 7387-7390.
17. Wakamiya, T., Ueki, Y., Shiba, T., Kido, Y., Motoki, Y. *Tetrahedron Lett* (1985) 26, 665-668.
18. Paik, S. H., Hansen, J. N. *GenBank* (1997) Accession Number AF014938.
19. Meyer, C., Bierbaum, G., Heidrich, C., Reis, M., Suling, J., Iglesias-Wind, M. I., Kempter, C., Molitor, E., Sahl, H. -G. *Eur. J. Biochem.* (1995) 232, 478-489.
20. Havarstein, L. S., Diep, D. B., Nes, I. F. *Mol. Microhiol.* (1995) 16, 229-240.
21. Fisk, C. L. (1975) Ph.D. Thesis, Georgetown University, Washington, D.C.
22. Jones, A. J., Helmerhorst, E., Stokes, G. B. *Biochem. J.* (1983) 211, 499-502.
23. Asquith, R. S., Carthew, P. *Tetrahedron* (1972) 28, 4769-4773.
24. Buchman, G. W., Banerjee, S., Hansen, J. N. *J. Biol. Chem.* (1988) 263,16260-16266.
25. Kupke, T., Stevanovic, S., Sahl, H. G., Gotz, F. *J. Bacteriol.* (1992) 174, 5354-5361.
26. Cleeland, R., Squires, E. (1991) in *Antibiotics in Laboratory Medicine* (Lorian, V., ed), pp 739-786, Williams & Wilkins: Baltimore, Md.,
27. Liu, W., Hansen, J. N. *Appl. Environ. Microbiol.* (1993) 59, 648-651.

28. Chan, W. C., Dodd, H. M., Horn, N., Maclean, K., Lian, L. Y., Bycroft, B. W., Gasson, M. J., Roberts, G. C. *Appl. Environ. Microbiol.* (1996) 62, 2966-2969.

29. Morris, S. L., Walsh, R. C., Hansen, J. N. *J. Biol. Chem.* (1984) 259, 13590-13594.

30 Buchman, G. W. (1988) Ph.D. Thesis, University of Maryland, College Park, Md.

31. Liu, W., Hansen, J. N. *Appl. Environ. Microbiol.* (1990) 56, 2551-2558.

32. Hancock, R. *Lancet* (1997) 349, 418-422.

33. Hancock, R., Falla, T. J. (1997) in *Biotechnology of Antibiotics*, Second ed. (Strohl, W. R., ed), pp 471-496, Marcel Dekker, Inc.: New York, 34. Chan, W. C., Bycroft, B. W., Leyland, M. L., Lian, L. Y., Roberts, G. C. *Biochemistry Journal* (1993) 291, 23-27.

35. Rosenberg, M., Court, D. *Ann. Rev. Genetics* (1979) 13, 319-353.

36. Kozak, M. *Microbiol. Rev.* (1983) 47, 1-45.

What is claimed is:

1. A method for inhibiting the spore outgrowth of gram positive bacteria comprising contacting said bacteria with a composition comprising an isolated peptide having the amino acid sequence of SEQ ID NO:18.

2. A method for inhibiting the spore outgrowth of gram positive bacteria comprising contacting said bacteria with a composition comprising an isolated peptide having the amino acid sequence of SEQ ID NO:18, and wherein the composition further comprises an active agent selected from the group consisting of a lantibiotic and an antibiotic.

3. A preserved food, comprising a food and a bacterial-growth-inhibiting effective amount of an isolated peptide having the amino acid sequence of SEQ ID NO:18.

4. A composition suitable for killing or inhibiting growth of bacteria, comprising an isolated peptide having the amino acid sequence of SEQ ID NO:18 and a carrier.

5. A composition suitable for killing or inhibiting growth of bacteria, comprising an isolated peptide having the amino acid sequence of SEQ ID NO:18, an active agent selected from the group consisting of a lantibiotic and an antibiotic, and a carrier.

6. The composition of claim 5, wherein the active agent is nisin.

7. The composition of claim 5, wherein the active agent is subtilin.

* * * * *

SEQUENCE LISTING

```
<160> NUMBER OF SEQ ID NOS: 18

<210> SEQ ID NO 1
<211> LENGTH: 48
<212> TYPE: DNA
<213> ORGANISM: Artificial Sequence
<220> FEATURE:
<221> NAME/KEY: modified_base
<222> LOCATION: (19)
<223> OTHER INFORMATION: adenine is modifed to inosine
<220> FEATURE:
<221> NAME/KEY: modified_base
<222> LOCATION: (20)
<223> OTHER INFORMATION: adenine is modifed to inosine
<220> FEATURE:
<221> NAME/KEY: modified_base
<222> LOCATION: (21)
<223> OTHER INFORMATION: adenine is modifed to inosine
<220> FEATURE:
<221> NAME/KEY: modified_base
<222> LOCATION: (40)
<223> OTHER INFORMATION: adenine is modifed to inosine
<220> FEATURE:
<221> NAME/KEY: modified_base
<222> LOCATION: (41)
<223> OTHER INFORMATION: adenine is modifed to inosine
<221> NAME/KEY: modified_base
<222> LOCATION: (42)
<223> OTHER INFORMATION: adenine is modifed to inosine
<220> FEATURE:
<223> OTHER INFORMATION: Description of Artificial Sequence: Probe

<400> SEQUENCE: 1
gggttgggta aagcccaann ngcggccttg tggttacagn nngcttcc            48

<210> SEQ ID NO 2
<211> LENGTH: 48
<212> TYPE: DNA
<213> ORGANISM: Artificial Sequence
<220> FEATURE:
<221> NAME/KEY: modified_base
<222> LOCATION: (19)
<223> OTHER INFORMATION: adenine is modifed to inosine
<220> FEATURE:
<221> NAME/KEY: modified_base
<222> LOCATION: (20)
<223> OTHER INFORMATION: adenine is modifed to inosine
<220> FEATURE:
<221> NAME/KEY: modified_base
<222> LOCATION: (21)
<223> OTHER INFORMATION: adenine is modifed to inosine
<220> FEATURE:
<221> NAME/KEY: modified_base
<222> LOCATION: (40)
<223> OTHER INFORMATION: adenine is modifed to inosine
<220> FEATURE:
<221> NAME/KEY: modified_base
<222> LOCATION: (41)
<223> OTHER INFORMATION: adenine is modifed to inosine
<221> NAME/KEY: modified_base
<222> LOCATION: (42)
<223> OTHER INFORMATION: adenine is modifed to inosine
```

```
<220> FEATURE:
<223> OTHER INFORMATION: Description of Artificial Sequence: Probe

<400> SEQUENCE: 2
gggttgggca aagcacagnn ngcggctttt tggttacagn nngcgtgc                    48

<210> SEQ ID NO 3
<211> LENGTH: 48
<212> TYPE: DNA
<213> ORGANISM: Artificial Sequence
<220> FEATURE:
<221> NAME/KEY: modified_base
<222> LOCATION: (19)
<223> OTHER INFORMATION: adenine is modifed to inosine
<220> FEATURE:
<221> NAME/KEY: modified_base
<222> LOCATION: (20)
<223> OTHER INFORMATION: adenine is modifed to inosine
<220> FEATURE:
<221> NAME/KEY: modified_base
<222> LOCATION: (21)
<223> OTHER INFORMATION: adenine is modifed to inosine
<220> FEATURE:
<221> NAME/KEY: modified_base
<222> LOCATION: (40)
<223> OTHER INFORMATION: adenine is modifed to inosine
<220> FEATURE:
<221> NAME/KEY: modified_base
<222> LOCATION: (41)
<223> OTHER INFORMATION: adenine is modifed to inosine
<221> NAME/KEY: modified_base
<222> LOCATION: (42)
<223> OTHER INFORMATION: adenine is modifed to inosine
<220> FEATURE:
<223> OTHER INFORMATION: Description of Artificial Sequence: Probe

<400> SEQUENCE: 3
ggacttggta aagcgcaann ngcagctctg tggcttcaan nngcatgc                   48

<210> SEQ ID NO 4
<211> LENGTH: 792
<212> TYPE: DNA
<213> ORGANISM: Bacillus subtilis 168
<220> FEATURE:
<221> NAME/KEY: CDS
<222> LOCATION: (219)..(389)
<220> FEATURE:
<221> NAME/KEY: CDS
<222> LOCATION: (447)..(782)

<400> SEQUENCE: 4
attattaatt caaaataaat ccataatagt caatttatt tagtgtatta caaccaattc        60
tgtttattga taggtaataa agttttttt ctatgattta tgaacaagtt tccttataat      120
tttcaaaaaa aaataaaaaa tatggttgaa tttagattta tcttccttta tattaaaaaa     180
tgtaatccgg attgcaaaca aatggggagg ttttacaa atg gaa aag cta ttt aaa      236
                                          Met Glu Lys Leu Phe Lys
                                            1               5 gaa gtt aaa cta gag gaa ctc gaa aac caa aaa ggt agt gga tta gga        284
Glu Val Lys Leu Glu Glu Leu Glu Asn Gln Lys Gly Ser Gly Leu Gly
             10                  15                  20 aaa gct cag tgt gct gcg ttg tgg cta caa tgt gct agt ggc ggt aca        332
Lys Ala Gln Cys Ala Ala Leu Trp Leu Gln Cys Ala Ser Gly Gly Thr
         25                  30                  35 att ggt tgt ggt ggc gga gct gtt gct tgt caa aac tat cgt caa ttc        380
Ile Gly Cys Gly Gly Gly Ala Val Ala Cys Gln Asn Tyr Arg Gln Phe
     40                  45                  50 tgc aga taa acatttgta gagggaatat tttaaatatt ccctcatatt                 429
Cys Arg *
```

```
Cys Arg
 55 taaagcgggg attgaaa ttg aat aag aaa aag aaa tat gtt cat act aaa        479
                    Met Asn Lys Lys Lys Lys Tyr Val His Thr Lys
                     60                  65 cag ttt aat agt cat gat tgt gga cta gct tgt atc tcg tca att tta      527
Gln Phe Asn Ser His Asp Cys Gly Leu Ala Cys Ile Ser Ser Ile Leu
 70                  75                  80 aag ttt cat aac ctt aac tat gga att gat ttc tta cta gac cta att      575
Lys Phe His Asn Leu Asn Tyr Gly Ile Asp Phe Leu Leu Asp Leu Ile
 85                  90                  95                 100 ggg gat aag gaa ggc tat agt tta aga gac tta att gtt att ttt aag      623
Gly Asp Lys Glu Gly Tyr Ser Leu Arg Asp Leu Ile Val Ile Phe Lys
                105                 110                 115 aag atg ggg ata aaa act agg cca ctt gaa ttg caa gaa aat aag aca      671
Lys Met Gly Ile Lys Thr Arg Pro Leu Glu Leu Gln Glu Asn Lys Thr
             120                 125                 130 ttc gaa gcc cta aaa caa ata aag ctc cct tgt ata gct ttg tta gaa      719
Phe Glu Ala Leu Lys Gln Ile Lys Leu Pro Cys Ile Ala Leu Leu Glu
             135                 140                 145 ggg gag gaa tat gga cat tac ata aca ata tac gaa att aga aat aac      767
Gly Glu Glu Tyr Gly His Tyr Ile Thr Ile Tyr Glu Ile Arg Asn Asn
 150                 155                 160 tat tta ctt gtt agt gatcctgata                                       792
Tyr Leu Leu Val Ser
 165

<210> SEQ ID NO 5
<211> LENGTH: 56
<212> TYPE: PRT
<213> ORGANISM: Bacillus subtilis 168
<220> FEATURE:
<223> OTHER INFORMATION: Pre-Sublancin 168

<400> SEQUENCE: 5

Met Glu Lys Leu Phe Lys Glu Val Lys Leu Glu Glu Leu Glu Asn Gln
 1               5                  10                  15

Lys Gly Ser Gly Leu Gly Lys Ala Gln Cys Ala Ala Leu Trp Leu Gln
                20                  25                  30

Cys Ala Ser Gly Gly Thr Ile Gly Cys Gly Gly Gly Ala Val Ala Cys
            35                  40                  45

Gln Asn Tyr Arg Gln Phe Cys Arg
        50                  55

<210> SEQ ID NO 6
<211> LENGTH: 112
<212> TYPE: PRT
<213> ORGANISM: Bacillus subtilis 168

<400> SEQUENCE: 6

Met Asn Lys Lys Lys Lys Tyr Val His Thr Lys Gln Phe Asn Ser His
 1               5                  10                  15

Asp Cys Gly Leu Ala Cys Ile Ser Ser Ile Leu Lys Phe His Asn Leu
                20                  25                  30

Asn Tyr Gly Ile Asp Phe Leu Leu Asp Leu Ile Gly Asp Lys Glu Gly
            35                  40                  45

Tyr Ser Leu Arg Asp Leu Ile Val Ile Phe Lys Lys Met Gly Ile Lys
        50                  55                  60

Thr Arg Pro Leu Glu Leu Gln Glu Asn Lys Thr Phe Glu Ala Leu Lys
 65                  70                  75                  80
```

Gln Ile Lys Leu Pro Cys Ile Ala Leu Leu Glu Gly Glu Tyr Gly
                85                  90                  95

His Tyr Ile Thr Ile Tyr Glu Ile Arg Asn Asn Tyr Leu Leu Val Ser
                100                 105                 110

<210> SEQ ID NO 7
<211> LENGTH: 37
<212> TYPE: PRT
<213> ORGANISM: Bacillus subtilis 168
<220> FEATURE:
<223> OTHER INFORMATION: Prosublancin 168

<400> SEQUENCE: 7

Gly Leu Gly Lys Ala Gln Cys Ala Ala Leu Trp Leu Gln Cys Ala Ser
1               5                   10                  15

Gly Gly Thr Ile Gly Cys Gly Gly Gly Ala Val Ala Cys Gln Asn Tyr
                20                  25                  30

Arg Gln Phe Cys Arg
            35

<210> SEQ ID NO 8
<211> LENGTH: 57
<212> TYPE: PRT
<213> ORGANISM: Unknown
<220> FEATURE:
<223> OTHER INFORMATION: Nisin A

<400> SEQUENCE: 8

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
                20                  25                  30

Gly Cys Lys Thr Gly Ala Leu Met Gly Cys Asn Met Lys Thr Ala Thr
            35                  40                  45

Cys His Cys Ser Ile His Val Ser Lys
        50                  55

<210> SEQ ID NO 9
<211> LENGTH: 56
<212> TYPE: PRT
<213> ORGANISM: Unknown
<220> FEATURE:
<223> OTHER INFORMATION: subtilin

<400> SEQUENCE: 9

Met Ser Lys Phe Asp Asp Phe Asp Leu Asp Val Val Lys Val Ser Lys
1               5                   10                  15

Gln Asp Ser Lys Ile Thr Pro Gln Trp Lys Ser Glu Ser Leu Cys Thr
                20                  25                  30

Pro Gly Cys Val Thr Gly Ala Leu Gln Thr Cys Phe Leu Gln Thr Leu
            35                  40                  45

Thr Cys Asn Cys Lys Ile Ser Lys
        50                  55

<210> SEQ ID NO 10
<211> LENGTH: 52
<212> TYPE: PRT
<213> ORGANISM: Unknown
<220> FEATURE:
<223> OTHER INFORMATION: epidermin

<400> SEQUENCE: 10

```
Met Glu Ala Val Lys Glu Lys Asn Asp Leu Phe Asn Leu Asp Val Lys
  1               5                  10                  15

Val Asn Ala Lys Glu Ser Asn Asp Ser Gly Ala Glu Pro Arg Ile Ala
             20                  25                  30

Ser Lys Phe Ile Cys Thr Pro Gly Cys Ala Lys Thr Gly Ser Phe Asn
         35                  40                  45

Ser Tyr Cys Cys
         50

<210> SEQ ID NO 11
<211> LENGTH: 60
<212> TYPE: PRT
<213> ORGANISM: Unknown
<220> FEATURE:
<223> OTHER INFORMATION: Pep5

<400> SEQUENCE: 11

Met Lys Asn Asn Lys Asn Leu Phe Asp Leu Glu Ile Lys Lys Glu Thr
  1               5                  10                  15

Ser Gln Asn Thr Asp Glu Leu Glu Pro Gln Thr Ala Gly Pro Ala Ile
             20                  25                  30

Arg Ala Ser Val Lys Gln Cys Gln Lys Thr Leu Lys Ala Thr Arg Leu
         35                  40                  45

Phe Thr Val Ser Cys Lys Gly Lys Asn Gly Cys Lys
         50                  55                  60

<210> SEQ ID NO 12
<211> LENGTH: 51
<212> TYPE: PRT
<213> ORGANISM: Unknown
<220> FEATURE:
<223> OTHER INFORMATION: Lacticin 481

<400> SEQUENCE: 12

Met Lys Glu Gln Asn Ser Phe Asn Leu Leu Gln Glu Val Thr Glu Ser
  1               5                  10                  15

Glu Leu Asp Leu Ile Leu Gly Ala Lys Gly Gly Ser Gly Val Ile His
             20                  25                  30

Thr Ile Ser His Glu Cys Asn Met Asn Ser Trp Gln Phe Val Phe Thr
         35                  40                  45

Cys Cys Ser
         50

<210> SEQ ID NO 13
<211> LENGTH: 51
<212> TYPE: PRT
<213> ORGANISM: Streptococcus pyogenes
<220> FEATURE:
<223> OTHER INFORMATION: Streptococcin A-FF22

<400> SEQUENCE: 13

Met Glu Lys Asn Asn Glu Val Ile Asn Ser Ile Gln Glu Val Ser Leu
  1               5                  10                  15

Glu Glu Leu Asp Gln Ile Ile Gly Ala Gly Lys Asn Gly Val Phe Lys
             20                  25                  30

Thr Ile Ser His Glu Cys His Leu Asn Thr Trp Ala Phe Leu Ala Thr
         35                  40                  45

Cys Cys Ser
         50
```

```
<210> SEQ ID NO 14
<211> LENGTH: 51
<212> TYPE: PRT
<213> ORGANISM: Unknown
<220> FEATURE:
<223> OTHER INFORMATION: Salivaricin A

<400> SEQUENCE: 14

Met Asn Ala Met Lys Asn Ser Lys Asp Ile Leu Asn Asn Ala Ile Glu
 1               5                  10                  15

Glu Val Ser Glu Lys Glu Leu Met Glu Val Ala Gly Gly Lys Arg Gly
                20                  25                  30

Ser Gly Trp Ile Ala Thr Ile Thr Asp Asp Cys Pro Asn Ser Val Phe
            35                  40                  45

Val Cys Cys
        50

<210> SEQ ID NO 15
<211> LENGTH: 68
<212> TYPE: PRT
<213> ORGANISM: Unknown
<220> FEATURE:
<223> OTHER INFORMATION: Cytolysin L1

<400> SEQUENCE: 15

Met Glu Asn Leu Ser Val Val Pro Ser Phe Glu Glu Leu Ser Val Glu
 1               5                  10                  15

Glu Met Glu Ala Ile Gln Gly Ser Gly Asp Val Gln Ala Glu Thr Thr
                20                  25                  30

Pro Val Cys Ala Val Ala Ala Thr Ala Ala Ala Ser Ser Ala Ala Cys
            35                  40                  45

Gly Trp Val Gly Gly Gly Ile Phe Thr Gly Val Thr Val Val Val Ser
         50                  55                  60

Leu Lys His Cys
 65

<210> SEQ ID NO 16
<211> LENGTH: 181
<212> TYPE: PRT
<213> ORGANISM: Unknown
<220> FEATURE:
<223> OTHER INFORMATION: LcnDR3

<400> SEQUENCE: 16

Met Lys Ile Val Leu Gln Asn Asn Glu Gln Asn Cys Leu Leu Ala Cys
 1               5                  10                  15

Tyr Ser Met Ile Leu Gly Tyr Phe Gly Arg Asp Val Ala Ile His Glu
                20                  25                  30

Leu Tyr Ser Gly Glu Met Ile Pro Pro Asp Gly Leu Ser Val Ser Tyr
            35                  40                  45

Leu Lys Asn Ile Asn Met Lys His Gln Val Ser Met His Val Tyr Lys
         50                  55                  60

Thr Asp Lys Lys Asn Ser Pro Asn Lys Ile Phe Tyr Pro Lys Met Leu
 65                  70                  75                  80

Pro Val Ile Ile Gln Trp Asn Asp Asn His Phe Val Val Thr Lys
                85                  90                  95

Ile Tyr Arg Lys Asn Val Thr Leu Ile Asp Pro Ala Ile Gly Lys Val
            100                 105                 110

Lys Tyr Asn Tyr Asn Asp Phe Met Lys Lys Phe Ser Gly Tyr Ile Ile
```

```
                    115                 120                 125
Thr Leu Ser Pro Asn Ser Ser Phe Thr Lys Lys Arg Ile Ser Glu
        130                 135                 140

Ile Ile Phe Pro Leu Lys Lys Ile Phe Lys Asn Arg Asn Thr Phe Leu
145                 150                 155                 160

Tyr Ile Phe Ser Leu Phe Ile Ser Gln Ile Val Ala Leu Trp Phe Ser
                165                 170                 175

Ile Ile Leu Arg Asp
            180

<210> SEQ ID NO 17
<211> LENGTH: 47
<212> TYPE: PRT
<213> ORGANISM: Unknown
<220> FEATURE:
<223> OTHER INFORMATION: PepT

<400> SEQUENCE: 17

Met Lys Lys Glu Asn Pro Leu Phe Phe Leu Phe Ser Lys Ile Lys Trp
  1               5                  10                  15

Pro Lys Ser Leu Phe Ile Ile Ala Ile Ile Ser Ser Ile Gly Ser
                20                  25                  30

Ile Thr Glu Ile Ile Val Pro Leu Leu Thr Gly Asn Leu Ile Asp
            35                  40                  45

<210> SEQ ID NO 18
<211> LENGTH: 37
<212> TYPE: PRT
<213> ORGANISM: Bacillus subtilis 168
<220> FEATURE:
<221> NAME/KEY: DISULFID
<222> LOCATION: (14)..(29)
<220> FEATURE:
<221> NAME/KEY: DISULFID
<222> LOCATION: (7)..(36)
<220> FEATURE:
<221> NAME/KEY: MOD_RES
<222> LOCATION: (16)
<223> OTHER INFORMATION: Xaa is a dehydrogenated Ser (Dha)
<220> FEATURE:
<221> NAME/KEY: THIOETH
<222> LOCATION: (19)..(22)
<220> FEATURE:
<221> NAME/KEY: MOD_RES
<222> LOCATION: (19)
<223> OTHER INFORMATION: Xaa is a dehydrogenated Thr (Dhb)

<400> SEQUENCE: 18

Gly Leu Gly Lys Ala Gln Cys Ala Ala Leu Trp Leu Gln Cys Ala Xaa
  1               5                  10                  15

Gly Gly Xaa Ile Gly Cys Gly Gly Gly Ala Val Ala Cys Gln Asn Tyr
                20                  25                  30

Arg Gln Phe Cys Arg
            35
```